(12) United States Patent  
Van Tilburg

(10) Patent No.: US 6,746,435 B1  
(45) Date of Patent: *Jun. 8, 2004

(54) SHAPED SANITARY NAPKIN WITH FLAPS

(75) Inventor: Kees J. Van Tilburg, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1212 days.

This patent is subject to a terminal disclaimer.

(21) Appl. No.: 08/570,281

(22) Filed: Dec. 11, 1995

Related U.S. Application Data

(63) Continuation of application No. 08/160,522, filed on Dec. 1, 1993, now Pat. No. 5,489,283, which is a division of application No. 07/054,716, filed on May 22, 1987, now Pat. No. 5,267,992, which is a continuation of application No. 06/789,914, filed on Oct. 17, 1985, now Pat. No. 4,687,478, which is a continuation of application No. 06/591,620, filed on Mar. 20, 1984, now abandoned, which is a continuation-in-part of application No. 06/511,118, filed on Jul. 5, 1983, now abandoned.

(51) Int. Cl.[7] ................................. A61F 13/15  
(52) U.S. Cl. ............. 604/385.04; 604/387; 604/385.01; 604/389  
(58) Field of Search ................ 604/385.1, 389, 604/390, 385.04

(56) References Cited

U.S. PATENT DOCUMENTS

| | | |
|---|---|---|
| 951,184 A | 3/1910 | Gillam |
| 2,102,359 A | 12/1937 | Frieman |
| 2,408,508 A | 10/1946 | Canavan |
| 2,735,109 A | 2/1956 | Feldman |
| 2,787,271 A | 4/1957 | Clark |
| 2,890,701 A | 6/1959 | Weinman |
| 3,082,437 A | 3/1963 | Upthagrove |
| 3,343,543 A | 9/1967 | Glassman |
| 3,397,697 A | 8/1968 | Rickard |
| 3,400,718 A | 9/1968 | Saijo |
| 3,595,235 A | 7/1971 | Jespersen |
| 3,613,686 A | 10/1971 | Waskin |
| 3,744,494 A | 7/1973 | Marsan |
| 3,881,490 A | 5/1975 | Whitehead et al. |
| 3,973,567 A | 8/1976 | Srinivasan et al. |
| 4,023,570 A | 5/1977 | Chinai et al. |
| D247,372 S | 2/1978 | Whitehead |
| 4,285,343 A | 8/1981 | McNair |
| 4,327,728 A | 5/1982 | Elias |
| 4,327,732 A | 5/1982 | Thinnes |
| 4,389,211 A | 6/1983 | Lenaghan |
| 4,391,869 A | 7/1983 | Cook et al. |
| 4,392,862 A | 7/1983 | Marsan et al. |
| 4,402,689 A | 9/1983 | Baum |
| 4,425,130 A | 1/1984 | DesMarais |
| 4,496,359 A | 1/1985 | Pigneul |
| 4,540,415 A | 9/1985 | Korpman |
| 4,551,143 A | 11/1985 | Cook et al. |
| 4,589,876 A | 5/1986 | Van Tilburg |
| 4,608,047 A | 8/1986 | Mattingly |
| 4,687,478 A | 8/1987 | Van Tilburg |
| 4,701,178 A | 10/1987 | Glaug et al. |
| 4,900,320 A | 2/1990 | McCoy |

FOREIGN PATENT DOCUMENTS

| | | |
|---|---|---|
| GB | 2 048 684 | 12/1980 |
| JP | 40-36391 | 12/1965 |
| JP | 46-12554 | 5/1971 |
| JP | 50-100399 | 8/1975 |
| JP | 50-44720 | 12/1975 |
| JP | 50-107718 | 4/1976 |
| JP | 52-117394 | 9/1977 |
| JP | 54-154696 | 4/1978 |
| JP | 55-16135 | 2/1980 |
| JP | 52758 | 4/1980 |
| JP | 57-20172 | 4/1982 |

*Primary Examiner*—John J. Calvert  
*Assistant Examiner*—Michele Kidwell  
(74) *Attorney, Agent, or Firm*—Steven W. Miller

(57) ABSTRACT

A shaped sanitary napkin. The sanitary napkin of this invention has an absorbent means, such as an absorbent core, and two flaps extending outwardly from the absorbent means. Each flap is associated with the absorbent means along a nonlinear line of juncture and each has two axes of flexibility. In use, the absorbent means is secured in the crotch of a panty and the flaps are secured about the elastic edges of the panty so that, when the panty is worn, the absorbent means is held adjacent the body while the flaps form a wall at each side of the absorbent means and seals against the body. Both the walls and the seals serve to prevent soiling of the body and clothing by menstrual fluid.

33 Claims, 4 Drawing Sheets

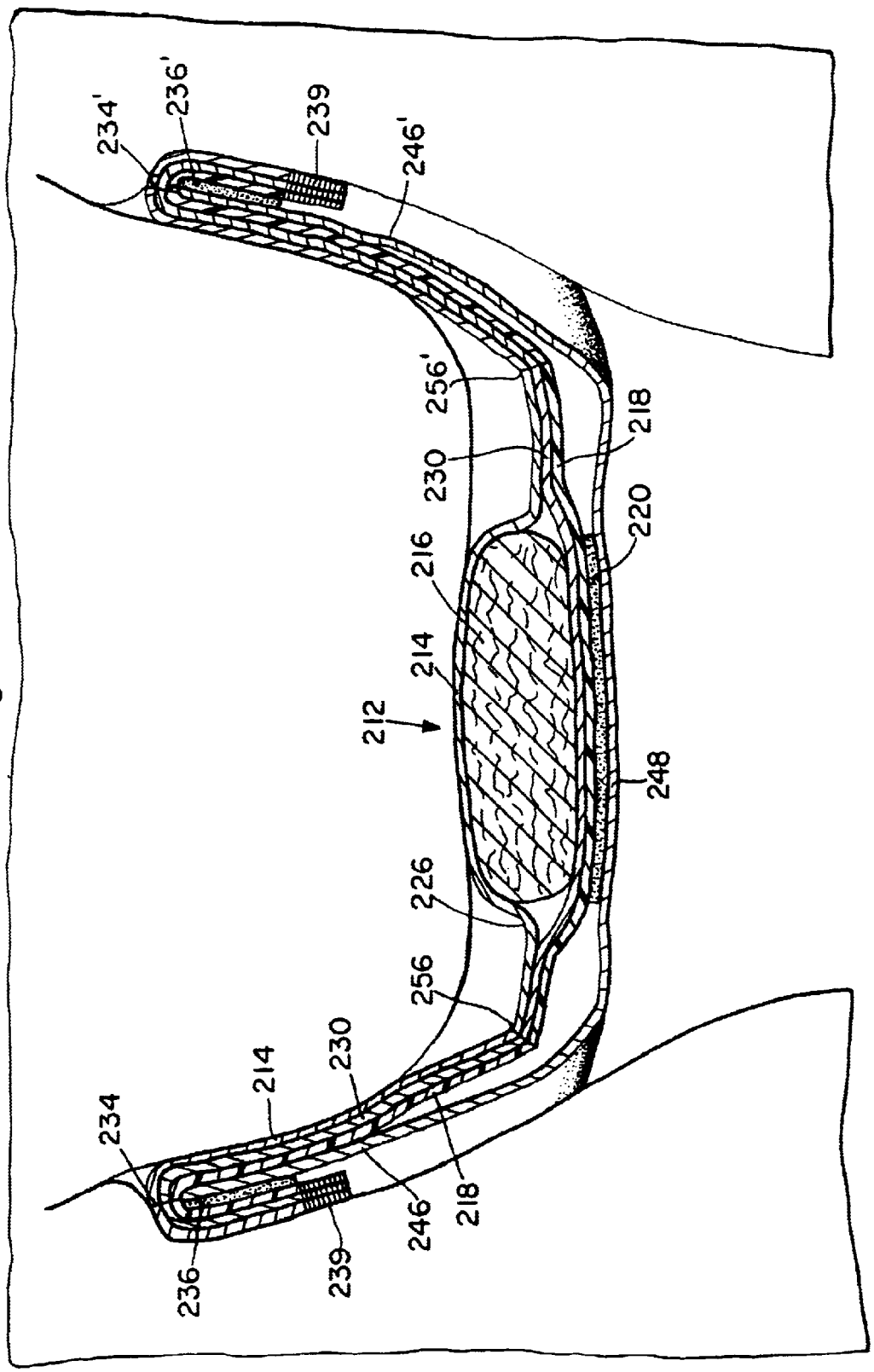

SHAPED SANITARY NAPKIN WITH FLAPS

This application is a continuation of application Ser. No. 08/160,522, filed on Dec. 1, 1993, now U.S. Pat. No. 5,489,283; which is a division of application Ser. No. 07/054,716, filed on May 22, 1987, now U.S. Pat. No. 5,267,992; which is a continuation of application Ser. No. 06/789,914, filed on Oct. 17, 1985, now U.S. Pat. No. 4,687,478; which is a continuation of application Ser. No. 06/591,620, filed on Mar. 20, 1984, now abandoned; which is a continuation-in-part of application Ser. No. 06/511,118, filed on Jul. 5, 1983, now abandoned.

BACKGROUND OF THE INVENTION

1. Field of the Invention

This invention relates to absorbent devices. More particularly, it relates to sanitary napkins.

2. Background Art

Sanitary napkins are absorbent devices designed to receive and contain vaginal discharges such as menses. They are omnipresent items of modern society. In recent periods disposable sanitary napkins designed to be held adjacent to the human body through the agency of a garment, such as an undergarment or panty, have effectively supplanted the more traditional type of sanitary napkin which required a specially designed belt for use.

Clark, in U.S. Pat. No. 2,787,271 issued on Apr. 2, 1957, describes a sanitary napkin comprising a rectangular central pad and a pair of lateral flaps fabricated integrally with the pad. These flaps are adapted to fold downwardly and bear against the opposed inner surfaces of the thighs of the wearer to arrest any overflow from the central pad which would normally stain clothing. This sanitary napkin is so fabricated that the lateral flaps will bend downwardly along straight parallel hinge lines defining the respective sides of the central pad. The central pad has a core body which is a soft, absorbent, fibrous material, such as absorbent cotton, and which extends without interruption into the lateral flaps. The hinges are formed by compressing (as by steam pressing with relatively sharp-edged pressing tools) along the lateral margins of the core body in the central pad.

Rickard, in U.S. Pat, No. 3,397,697 issued Aug. 20, 1968, describes a disposable sanitary shield for undergarments. This device comprises an elongate sheet of flexible material divided into at least two panels which are joined by an intermediate neck-like portion. The edge portions of one of the panels adjacent the neck-like portion comprises opposed wing-like flaps adapted to be folded over each other and to confine and encircle the crotch portion of a panty undergarment. The width of the crotch portion of the panty is thus restricted by an encircling absorbent band which is in freely slideable relationship with the crotch portion of the panty.

McNair, in U.S. Pat. No. 4,285,343 issued Aug. 25, 1981, describes a sanitary napkin comprising a central elongate absorbent pad element having side panels extending laterally therefrom. The side panels may be formed either integrally with the central element or they may be formed separately and secured to the longitudinal edges of the central absorbent pad. Lines of common juncture between the central element and the side panels must be flexible so that each side panel can be folded about the respective lateral edge of the central absorbent pad and toward the backside of the central element when the device is used. In use, the central element is adhesively secured to the innerside of the crotch portion of the undergarment and each side panel is folded over to encompass at least half of the outer surface of the crotch portion of the undergarment.

SUMMARY OF THE INVENTION

The present invention is of an absorbent device comprising an absorbent means and two flaps extending outwardly from the absorbent means. Each of the flaps is associated with the absorbent means along a nonlinear line of juncture and has a free distal edge remote from the line of juncture. Each of the flaps includes two axes of flexibility; the first is intermediate the line of juncture and the distal edge while the second is intermediate the first axis and the distal edge.

A preferred embodiment of the present invention is a sanitary napkin comprising an absorbent means having two opposed longitudinal edges, a fluid pervious body contacting surface, and an opposed liquid impervious surface. It also comprises two flaps, one extends outwardly from each longitudinal edge of the absorbent means. Each of the flaps is, as above, associated with the absorbent means along a nonlinear line of juncture and has a free distal edge remote from the line of juncture. Each of the flaps includes two axes of flexibility; the first is intermediate the line of juncture and the distal edge while the second is intermediate the first axis and the distal edge. The first axis is adapted to allow independent rotation of the distal edge of the flap in an arc generally in the direction from the liquid impervious surface toward the fluid pervious body contacting surface while the second is adapted to allow rotation of the distal edge in an arc generally in the direction from the fluid pervious body contacting surface toward the liquid impervious surface.

In preferred embodiments, the flaps are flexible essentially over their entire surface thereby providing an infinite number of axes of flexibility. In other embodiments, at least one of the axes is uniquely defined by distinct structural features.

Optionally, and preferably, adhesive attachment means are provided on the absorbent means and each of the flaps to secure the device in the crotch portion of an undergarment.

BRIEF DESCRIPTION OF THE DRAWINGS

FIG. 7 is a fragmentary coronal view showing the sectioned sanitary napkin and panty of FIG. 6 in place on a user.

DETAILED DESCRIPTION OF THE INVENTION

While the present specification concludes with claims particularly pointing out and distinctly claiming that which is regarded as the invention, it is believed that the present invention can be more readily understood through study of the following specification and of the appended drawings.

Figure 1:
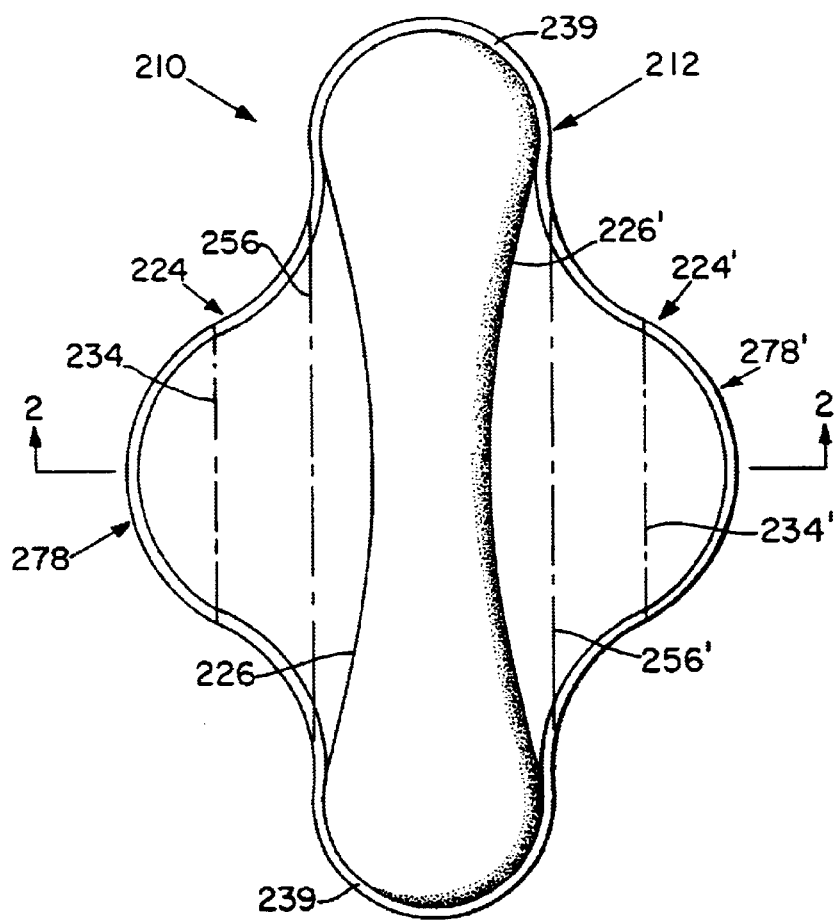
FIG. 1 is a plan view of a preferred embodiment of a sanitary napkin of the present invention.
Figure 2:
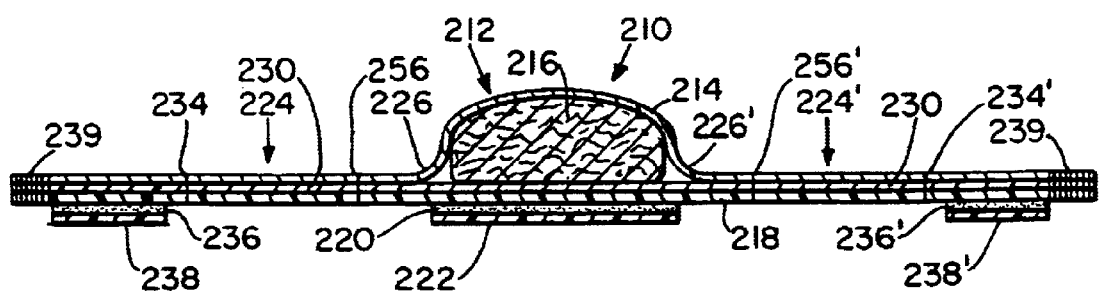
FIG. 2 is a cross sectional view of the sanitary napkin of FIG. 1 taken along line 2—2 of FIG. 1. The thicknesses of certain elements have been exaggerated for clarity.

A preferred embodiment of a sanitary napkin of the present invention is shown in FIGS. 1 and 2. Sanitary napkin 210 comprises an absorbent means represented by central absorbent pad 212 and two flaps 224 and 224'. (In the discussion that follows, unless otherwise noted, the sanitary napkins will have two flaps. While it is not necessary that the flaps be identical, or, more properly, mirror images one of the other, they preferably are. Thus the description of the first will be a description of the second. Discussion of the second will, therefore, be omitted for clarity of exposition. Corresponding elements are indicated in the drawings by reference numerals and primed reference numerals.)

Flap 224 is associated with central absorbent pad 212 along nonlinear line of juncture 226. As used in the context of the present specification, the term "nonlinear" refers to any of various curved, as opposed to straight, lines.

Flap 224 has distal edge 278 which is remote from line of juncture 226. In the embodiment illustrated in FIG. 1, line of junctue 226 is concave relative to distal edge 278. That is to say, line of juncture 226 curves away from distal edge 278. In this embodiment, nonlinear lines of juncture 226 and 226' and seam 239 define an absorbent means (central absorbent pad 212) which is narrower in its central region than at its ends. A sanitary napkin narrower in the center than at the ends is generally perceived by the user as more comfortable than a sanitary napkin of uniform width.

Flap 224 is provided with first axis of flexibility 256 and second axis of flexibility 234.

FIG. 2, a cross sectional view of sanitary napkin 210 taken along line 2—2, illustrates generally the preferred construction for sanitary napkin 210. As shown in FIG. 2, central absorbent pad 212 comprises absorbent core 216. Central absorbent pad 212 and flap 224 both comprise topsheet 214. Backsheet 218 is disposed on the side of absorbent core 216 and flap 224 opposite that of topsheet 214. In effect, topsheet 214 forms one surface of flap 224 while backsheet 218 forms the other surface: topsheet 214 also forms one surface of central absorbent pad 212, backsheet 218 the other.

In the embodiment illustrated, flap absorbent core 230 is interposed between topsheet 214 and backsheet 218. For simplicity of construction, flap absorbent core 230 extends throughout napkin 210 and is interposed between absorbent core 216 and backsheet 218. While this is a preferred embodiment primarily for reasons of construction, it is not necessary that flap absorbent core 230 be interposed between absorbent core 216 and backsheet 218.

Topsheet 214 and backsheet 218 are joined at seam 239 around the entire periphery of sanitary napkin 210. The purpose of this seam is to unite the various elements of the sanitary napkin into a whole. Topsheet 214 is secured to flap absorbent core 230 and backsheet 218 along nonlinear lines of juncture 226 and 226' by attachment means not illustrated in FIG. 2.

Illustrated in FIG. 2 are the adhesive attachment means central pad adhesive 220 and flap adhesive 236 which are covered by, respectively, central pad release liner 222 and flap release liner 238. These adhesive attachment means are adapted to secure sanitary napkin 210 within the crotch region of an undergarment.

Topsheet 214 is liquid permeable and, when sanitary napkin 210 is in use, is in close proximity to the skin of the user. Topsheet 214 is compliant, soft feeling and non-irritating to the user's skin. It can be made from any of the materials conventional for this type of use. Nonlimiting examples of suitable materials that can be used as topsheet 214 are woven and nonwoven polyester, polypropylene, nylon, and rayon and formed thermoplastic films; formed films are preferred. Suitable formed films are described in U.S. Pat. No. 4,324,246 issued to Mullane and Smith on Apr. 13, 1982 and U.S. Pat. No. 4,342,314 issued to Radel and Thompson on Aug. 3, 1982, both of which patents are incorporated herein by reference. Formed films are preferred for topsheet 214 because they are pervious to liquids and yet non-absorbent. Thus, the surface of the formed film, which is in contact with the body, remains dry and is more comfortable to the wearer.

In preferred embodiments of the present invention, the outer surface of topsheet 214 is treated with a surfactant. Treating the outer surface of the topsheet with surfactant renders the surface more hydrophilic which results in liquid penetrating the topsheet faster than if the surface were not treated. This diminishes the likelihood that menstrual fluid will flow off topsheet 214 rather than being absorbed by the absorbent core 216. It is preferred that the surfactant be substantially evenly and completely distributed across the outer surface of topsheet 214. This can be accomplished by any of the common techniques well known to those skilled in the art. For example, the surfactant can be applied to topsheet 214 by spraying, by padding, or by the use of transfer rolls.

In preferred embodiments, the inner surface of topsheet 214 is secured in contacting relation to absorbent core 216. This contacting relationship results in liquid penetrating topsheet 214 faster than if it were not in contact with absorbent core 216. Topsheet 214 can be maintained in contact with absorbent core 216 by applying adhesive, preferably in spaced, limited areas, to the inner surface of the topsheet 214. Examples of suitable adhesives used for this purpose include the acrylic emulsion E-1833BT manufactured by Rohm and Haas Company of Philadelphia, Penn. and the acrylic emulsion WB3805 manufactured by H. B. Fuller Company of St. Paul, Minn. The adhesives can be applied by the same methods as the surfactant is applied to the outer surface of topsheet 214.

Referring to FIG. 2, it can be seen that absorbent core 216 is positioned between topsheet 214 and backsheet 218. Absorbent core 216 provides the means for absorbing menstrual fluid. Absorbent core 216 is generally compressible, conformable, and non-irritating to the user's skin. It can comprise any material used in the art for such purpose. Examples of suitable materials are layers of tissue (such as wadding) and fibrated comminution pulp (airfelt), with fibrated comminution pulp being preferred.

Backsheet 218 is impervious to liquids and, thus, prevents menstrual fluid which may be expressed from absorbent core 216 from soiling the clothing of the user. Any material used in the art for such purpose can be utilized herein. Suitable materials are embossed or nonembossed polyethylene films and laminated tissue.

The outer surface of backsheet 218, generally in register with absorbent core 216, is coated with central pad adhesive 220. Central pad adhesive 220 provides an adhesive attachment means for securing central absorbent pad 212 in the crotch portion of a panty. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by National Starch Company. As shown in FIG. 2, central pad adhesive 220 is generally the same width as absorbent core 216; the width is not critical and appropriate widths, as well as lengths, can be readily selected by those skilled in the art. The pressure sensitive adhesive of central pad adhesive 220 should be covered with central pad release liner 222 to keep the adhesive from drying out and to keep it from sticking to extraneous surfaces prior to use. Any commercially available release liner commonly used for such purposes can be used herein. Nonlimiting examples of suitable release liners are BL 30 MG-A Silox E1/0 and BE 30 MG-A Silox 4 P/O both of which are manufactured by the Akrosil Corporation.

As can be observed from the foregoing discussion, central absorbent pad 212 is an absorbent means that has a fluid pervious body contacting surface (represented in FIG. 2 by topsheet 214) and an opposed liquid impervious surface (represented in FIG. 2 by backsheet 218). It is to be understood that the embodiment illustrated is only one possible embodiment, albeit a preferred one. Other possible embodiments include one in which an absorbent core is essentially completely wrapped with topsheet before it is placed on a backsheet. The absorbent means can also comprise an absorbent core which possesses sufficient integrity to stand alone and which is fluid permeable on one surface while the other surface has been treated to render it liquid impervious.

It should be noted that a narrow central absorbent pad 212 is effective because the overall configuration and use of sanitary napkin 210 results in central absorbent pad 212 being maintained in close proximity to the body. Such proximity of central absorbent pad 212 places it precisely where it should be: very near the body at the vaginal opening. Central absorbent pad 212 can then absorb the vast majority of the menstrual fluid (menses) before it has an opportunity to flow along central absorbent pad 212.

It is to be observed that lines of juncture 226 and 226' are the lines along which flaps 224 and 2241 are associated with the absorbent means (represented by central absorbent pad 212); as such they represent lines of demarcation between the absorbent means and the flaps. It is also to be observed that the lines of juncture are nonlinear. Preferably, they are concave relative to distal edges 278 and 278' and relative to the bulk of central absorbent pad 212. The absorbent means thus takes on a shape in which the width at its center is less than the width at its ends. This contoured shape is closely atuned to anatomical dimensions of the crotch region of the user. It makes the sanitary napkin more comfortable to wear while, at the same time, making it more effective as by rendering it less subject to compression by the legs of the user. While nonlinear lines of juncture which are convex relative to the distal edges and to the bulk of the central absorbent pad can be used, they are not preferred.

It is preferred that the width of central absorbent pad 212 between lines of juncture 226 and 226' at their nearest approach be from about 1 to about 8 centimeters. The width of the central absorbent pad 212 at its ends should be from about 2 to about 9 centimeters. Central absorbent pad 212 should be from about 7.6 to about 38 centimeters long.

Central absorbent pad 212 need not have an absorbent capacity much greater than the total amount of menstrual fluid anticipated to be absorbed. Thus, central absorbent pad 212, in addition to being narrow, can be relatively thin. Furthermore, a narrow and thin absorbent means is extremely comfortable to the user. In the embodiment illustrated in FIGS. 1 and 2, topsheet 214 serves as a topsheet for flaps 224 and 224'. In general, the flaps do not require a topsheet to enable them to function properly, but the use of a topsheet is preferred. Flap topsheets can be integral with the absorbent means' body contacting surface, as illustrated, or they can be independent elements; the former is preferred. All the specific physical property comments made above about topsheet 214 apply to any flap topsheet that is used.

There is, however, no requirement that the flap topsheet be the same material as the topsheet associated with the central absorbent pad. In preferred embodiments, the flap topsheet can be a nonwoven material while the topsheet with the central absorbent pad is a formed film.

Flap absorbent core 230 is positioned between topsheet 214 and backsheet 218, most importantly in flaps 224 and 224'. In the embodiment illustrated, flap absorbent core also underlies absorbent core 216; this is a preferred arrangement because construction of the sanitary napkin 210 is thereby facilitated. In this arrangement, the absorbent capacity of absorbent core 216 is enhanced. Flap absorbent core 230 provides a means for absorbing menstrual fluid that is not absorbed by, or that is expressed from, absorbent core 216. Flap absorbent core 230 is generally compressible, conformable and non-irritating to the user's skin. It can be made from any of the materials that can be used to make the absorbent core 216 as described above. Preferably, flap absorbent core 230 is a tissue paper sheet. While the use of a flap absorbent core is highly preferred, it can be omitted.

In the embodiment illustrated in FIGS. 1 and 2, backsheet 218 serves as a backsheet for flaps 224 and 224'. The flaps require a backsheet (or more generally, a liquid impervious material) to enable them to function properly. The flap backsheets can be integral with the absorbent means liquid impervious surface, as illustrated, or they can be independent elements; the former is preferred. All the specific physical property comments made above about backsheet 218 apply to any flap backsheet.

The overall size of flap 224 can be readily selected by those skilled in the art. Preferably, sanitary napkin 210 is from about 10 to about 23 centimeters wide between distal edges 278 and 278' at their greatest separation. Preferably flap 224 is from about 7.6 to about 18 centimeters long in the direction parallel to the longitudinal axis of the sanitary napkin.

The outer surface of flap 224, adjacent distal edge 278, is coated with flap adhesive 236.

Flap adhesive 236 is an adhesive attachment means which is used to assist in maintaining flap 224 in position after it is wrapped around the edge of the crotch portion of a panty as described below. Any adhesive used for central pad adhesive 220 can be used as flap adhesive 236. Also, flap adhesive 236 is covered with a removable flap release liner 238. Any release liner material used for central pad release liner 222 can be used for flap release liner 238.

As shown in FIGS. 1 and 2, topsheet 214 is secured to backsheet 218 along seam 239. Seam 239 can be formed by any means commonly used in the art for this purpose such as by gluing, crimping or heat sealing. Seam 239 is illustrated extending completely around the periphery of sanitary napkin 210; this is a preferred embodiment for ease of construction. (Other means of uniting the various elements of the device can be used.) Flap absorbent core 230 is illustrated as extending into seam 239; this is, likewise, an arrangement which results from a simplified construction technique. The three elements—topsheet, flap absorbent core, and backsheet—can be brought into register, with the absorbent core properly positioned between them, and the seam formed and the outer shape of the sanitary napkin established by cutting in one or two operations.

Topsheet 214 can be secured to backsheet 218 (and to flap absorbent core 230) along lines of juncture 226 and 226' by any of the techniques used to form seam 239.

Flap 224 contains first axis of flexibility 256 and second axis of flexibility 234. These two axes of flexibility allow flap 224 to form a wall, in use, as described hereinafter.

First axis of flexibility 256 is so constructed as to allow the flap to bend along first axis of flexiblity 256. The direction of the bend of the flap is upward when sanitary napkin 210 is in the configuration of FIG. 2. More generally, the direction of the bend is such that that portion of flap 224 containing distal edge 278 rotates about the first axis of flexibility 256 in an arc beginning generally from its extended position, as shown in FIG. 2, toward the fluid pervious body contacting surface of the absorbent means (as represented in FIG. 2 by that portion of topsheet 214 in register with absorbent core 216) and away from the liquid impervious surface of the absorbent means (as represented in FIG. 2 by that portion of backsheet 218 in register with absorbent core 216).

Second axis of flexibility 234 is so constructed as to allow the flap to bend along second axis of flexibility 234. The direction of the bend is downward when sanitary napkin 210 is in the configuration of FIG. 2. More generally, the direction of the bend is such that that portion of the flap 224 containing distal edge 278 rotates about second axis of flexibility 234 in an arc generally from its extended position, as shown in FIG. 2, toward the liquid impervious surface of the absorbent means (as represented in FIG. 2 by that portion of backsheet 218 in register with absorbent core 216 as comprising central absorbent pad 212) and away from the fluid pervious body contacting surface of the absorbent means (as represented in FIG. 2 by that portion of topsheet 214 in register with absorbent core 216).

First and second axes of flexibility can be provided in various ways. A preferred method is shown in FIGS. 1 and 2. In the embodiment illustrated, the materials of construction of flap 224 are selected so that flap 224 is extremely flexible over essentially the whole of its extent. Axes of flexibility of 256 and 234, as shown in FIGS. 1 and 2, are not, then, single, unique structures, but are, rather, representative of an essentially infinite number of pairs of axes. This arrangement is particularly preferred because it allows sanitary napkin 210 to be easily adjusted, during application, to properly fit a number of differently sized undergarments and, in use, anatomies as described below.

Total flexibility of flap 224 permits flap 224 to be positioned around the edge of the crotch portion of a panty without having to alter the natural path of the edge of the crotch portion of a panty. Thus, the edge of the crotch portion of a panty need not be stretched to fit to the second flexible axis of the flap. Furthermore, the natural path of the edge of the crotch portion of a panty results, when the sanitary napkin is in place for use, in the highest wall (described below) being formed; this, in turn, provides the greatest barrier to flow of the menstrual fluid.

In the embodiment of sanitary napkin 210 illustrated in FIGS. 1 and 2, it is preferred that the materials of construction of flap 224 be selected so that the flap has a resistance to bending, through an arc of 90°, of less than about 200 grams, more preferably less than about 50 grams, and most preferably less than about 25 grams as measured by the PCA Score Bend Tester manufactured by the Thwing-Albert Instrument Company of Philadelphia, Penn. These values are obtained when a section of flap 7.6 centimeters long (and which is maintained 2.5 centimeters above the bottom edge of the tilting plate of the tester) is evaluated under TAPPI standard conditions.

In the abstract, an axis is generally considered to be a linear element. The present axes of flexibility are also generally linear, but, since the materials from which the flaps are constructed generally possess such a degree of flexibility that the flaps can be bent and folded conveniently with manual force, the axes of flexibility can become nonlinear under the influence of external forces.

Figure 3:
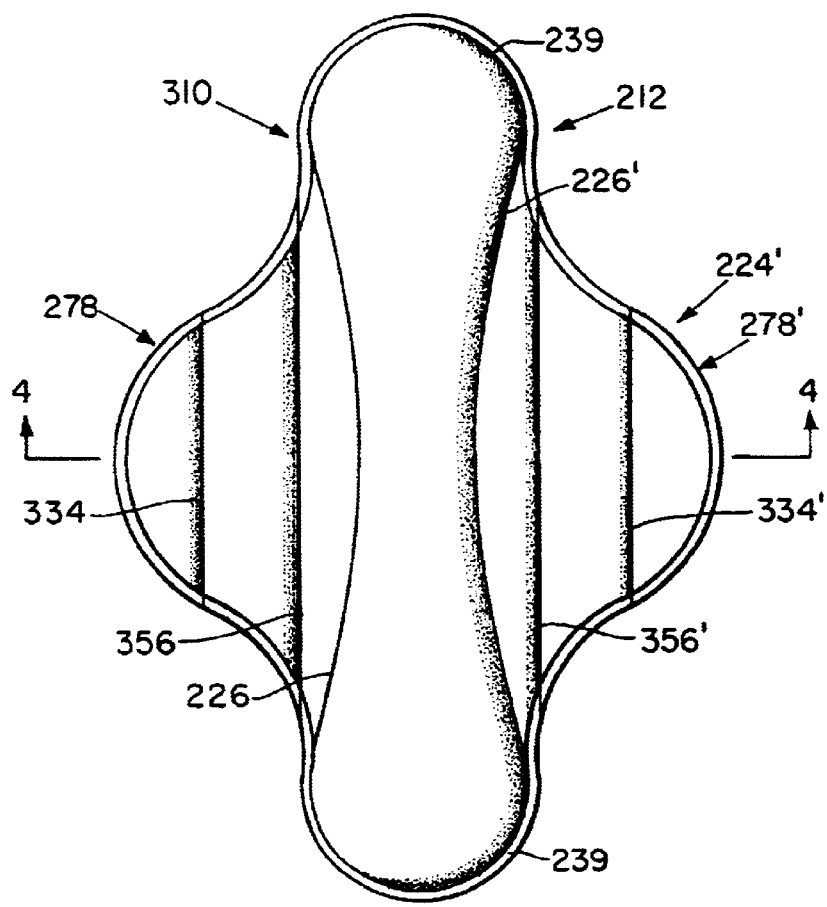
FIG. 3 is a plan view of an alternate embodiment of a sanitary napkin of the present invention.
Figure 4:
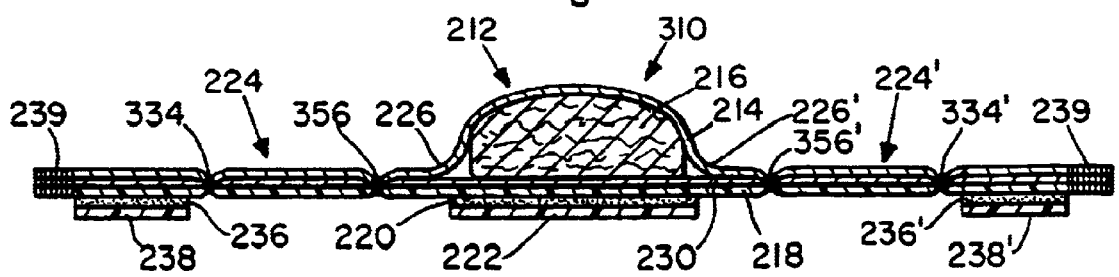
FIG. 4 is a cross sectional view of the sanitary napkin shown in FIG. 3 taken along line 4—4 of FIG. 3. The thicknesses of certain elements have been exaggerated for clarity.

An alternate embodiment of a sanitary napkin 310 having first and second axes of flexiblity 356 and 334 in flap 224 is illustrated in FIGS. 3 and 4. (The reference numerals used in FIGS. 3 and 4 refer to the same elements as in FIGS. 1 and 2.) In this embodiment, axes of flexibility 356 and 334 are provided by severely crimping flap 224 as illustrated. Thus, flap 224 of sanitary napkin 310 contains two unique axes (or unique hinge means) along which flap 224 can bend as described in relation to the embodiment shown in FIGS. 1 and 2. Axes of flexibility 356 and 356' preferably are from about 2 to about 18 centimeters apart. Axes of flexibility 234 and 256 (and 234' and 256') are preferably from about 1 to about 5 centimeters apart. While this is a satisfactory embodiment of the present invention, it is less preferred than the embodiment illustrated in FIGS. 1 and 2 because the crotch of the undergarment to which it is applied must. In general, be either stretched or compressed as sanitary napkin 310 is applied. Nevertheless, use of the embodiment illustrated in FIGS. 3 and 4 will result in one obtaining essentially all the benefits associated with the use of the embodiment illustrated in FIGS. 1 and 2.

As illustrated in FIG. 1, first axis of flexibility 256 is in close proximity to line of juncture 226. First axis of flexibility 256 can, in fact, intersect the line of juncture 226 at the point the latter contacts the outer margin of the sanitary napkin (as that margin is represented by seam 239). In the general case, this will be the only situation in which first axis of flexibility 256 and line of juncture 226 touch or coincide. It is to be understood, however, that application of external forces during use can cause the first axis of flexibility to be displaced toward the line of juncture so that, in some instances, the two can touch or coincide.

Sanitary napkins including the central absorbent pad comprising a liquid pervious topsheet, a liquid impervious backsheet, and an absorbent core interposed between the topsheet and the backsheet, and having a flap extending from each longitudinal edge of the central absorbent pad, wherein the line of juncture between each flap and the longitudinal edge of the central absorbent pad is linear, and having each flap provided with a flexible axis located in the body of the flap, can be constructed so that the sanitary napkin preferentially bends at the linear line of juncture of each flap and the longitudinal edge of the central absorbent pad as well as at the flexible axis located within the body of the flap. Such napkins, while distinctly different from those of the present invention, will function in a manner analogous to those of the present invention.

The precise shape of flap 224, as well as the overall shape of sanitary napkin 210, can be selected by those skilled in the art without undue experimentation. In the embodiments illustrated in FIGS. 1 and 3, the flaps are symmetrically disposed along the longitudinal axis of the sanitary napkin; while this is a preferred embodiment, it is not a mandatory design feature. As noted above, the flaps are generally mirror images one of the other; while such a situation is preferred, it is likewise not a mandatory design condition.

Further, the sanitary napkins illustrated in FIGS. 1 through 4 are embodiments wherein the flaps are formed integrally with the topsheets and backsheets of the sanitary napkin. Once again, while this is a preferred method of construction, it is not mandatory. Flaps and central absorbent means can be formed independently and joined by techniques well know to those skilled in the art in such a manner that the resulting sanitary napkin will function essentially equivalently to the embodiments illustrated herein.

In use, the sanitary napkins of this invention can be held in place by any support means well known for such purpose. Belts worn about the waist of the user can be used. It is highly preferred, however, that they be placed in the user's panty undergarment as described below.

Figure 5:
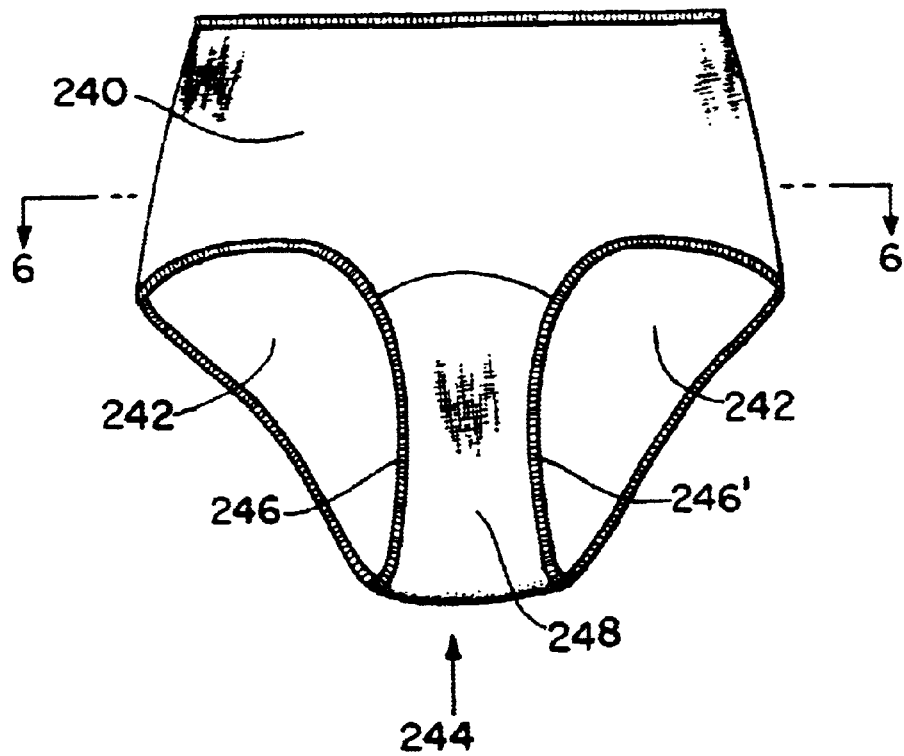
FIG. 5 is a front view of a conventional panty in which the sanitary napkin of the present invention can be used.

FIG. 5 is an undergarment of the type commonly worn by many women and well known as a panty. It comprises front section 240, back section 242, and crotch portion 244 which joins front and back sections 240 and 242. Crotch portion 244 comprises two side edges 246 and 246' and center crotch portion 248.

Figure 6:
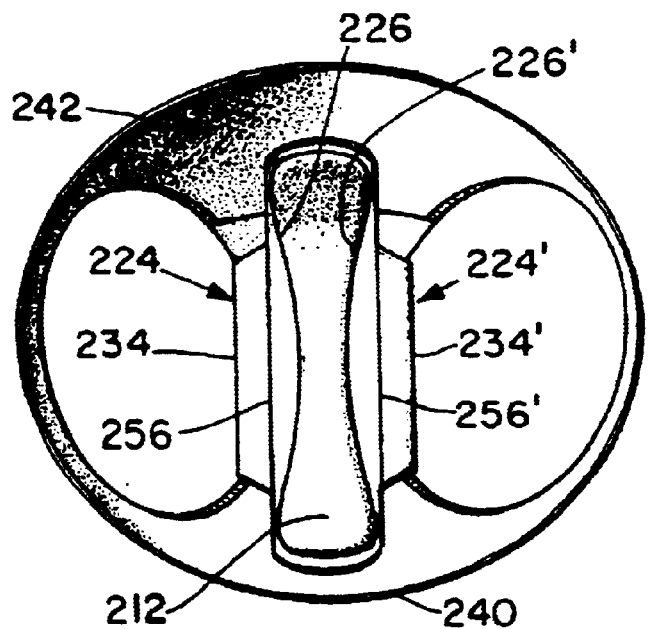
FIG. 6 is a cross sectional view of the panty of FIG. 5 taken along line 6—6 showing the sanitary napkin of FIG. 1 disposed therein.

A sanitary napkin of the present invention, such as the one illustrated at 210 in FIGS. 1 and 2, is utilized by removing the release liners 222, 238 and 238' and thereafter placing the sanitary napkin in a panty as shown in FIG. 6. The center of central absorbent pad 212 is placed in crotch portion 244 of the panty with one end of central absorbent pad 212 extending toward front section 240 and the other end toward back section 242 of the panty and with backsheet 218 in contact with the inner surface of center crotch portion 248 of the panty. Central pad adhesive 220 maintains central absorbent pad 212 in position. The distal portions of flaps 224 and 224' are folded around, respectively, side edges 246 and 246' of the panty by bending along second flexible axes 234 and 234'. Flap adhesive 236 and 236' secure flaps 224 and 224' in such position. Thus, flaps 224 and 224' are each folded over themselves with a portion of the panty—including side edges 246 and 246'—interposed therebetween.

Numerous benefits are derived from the use of the sanitary napkin of the present invention. Flaps 224 and 224' are wrapped around each edge 246 and 246' of the crotch portion 244 of the panty as shown in FIG. 6. This encapsulation of the panty crotch assists in preventing the menstrual fluid from coming into contact with the center crotch portion of the panty. Thus, the center crotch portion of the panty will not be soiled.

There are two other benefits. One is that the portions of the flaps containing the second axes of flexibility, 234 and 234', provide an excellent gasket-like seal against the body. The other is that the central absorbent means, such as central absorbent pad 212, is maintained in excellent contiguous relationship to the body.

The edge of the crotch portion of a panty generally contains an elastic material. When a panty is worn, the elastic of the edge of the crotch portion generates an upward force, i.e., against the body, due to the energy in the elastic and the fit of the panty. The placement of the second axis of flexibility, such as second axes of flexibility 234 and 234', between the body and the edges of the crotch portion of the panty results in the upward force generated by the edge of the crotch portion of the panty pushing the portion of the flaps containing the second axes of flexibility snugly against the body. This results in a gasket-like seal being formed along the axes of flexibility between the flaps and the body. This is illustrated in FIG. 7 which is a fragmentary coronal view showing the sectioned sanitary napkin and panty of FIG. 6 in place on a user. (A coronal view is the frontal plane that passes through the long axis of the body.) The gasket-like seal assists in preventing menstrual fluid from penetrating beyond the second axes of flexibility which, in turn, minimizes soiling of the legs and adjoining clothing. Another benefit derived from the flaps being pushed snugly against the body along the second axes of flexibility is that the absorbent means (central absorbent pad) is forced into close proximity to and into conformity with the body. This, too, is illustrated in FIG. 7. The maintenance of the central absorbent pad against the body is know as "good body contact". Good body contact is beneficial because it provides a barrier to lateral flow of menstrual fluid. Without such a barrier, menstrual fluid would tend to flow quickly along the topsheet, thereby providing less time for it to be absorbed by the absorbent core.

Inherent bunching is the formation of wrinkles along the lateral axes of a sanitary napkin resulting from the initial placement of the sanitary napkin in a panty for use. (Lateral axes of a sanitary napkin extend across the "crotch portion" of the napkin generally parallel to line 2—2 of FIG. 1.) This inherent bunching is due to the facts that a sanitary napkin is essentially linear along its longitudinal axis and that the anatomical contour of the body where the sanitary napkin is placed is essentially "U" shaped. (The longitudinal axis of a sanitary napkin extends from end to end of the central absorbent means and is generally perpendicular to line 2—2 of FIG. 1.) Thus, as soon as a sanitary napkin is put in place, its shape is changed along its longitudinal axis from being essentially linear to "U" shaped. This change in shape creates wrinkles along the lateral axes of the sanitary napkin, with the vast majority of the wrinkles being at the point of greatest curvature of the body i.e. the crotch area.

Forced bunching is the wrinkling of a sanitary napkin, along either its lateral or longitudinal axes, caused by movement of the legs of the user.

Wrinkles in a sanitary napkin created by inherent and forced bunching are known as flow channels because menstrual fluid can easily flow along the trough of the wrinkle in the absence of significant body contact along the wrinkle.

The sanitary napkin of the present invention provides numerous benefits because the flaps bend at the first axis of flexibility. In particular, the benefits provided are that:

(1) inherent bunching results in flow channels being formed substantially only in the central absorbent pad, not the bulk of the flaps;

(2) the sanitary napkin of the present invention can withstand much forced bunching before flow channels are created;

(3) even if the forced bunching is harsh enough to create flow channels, the channels formed will be essentially limited to the central absorbent pad; and (4) even if the forced bunching is so great that flow channels are created in both the central absorbent pad and the flaps, the menstrual fluid is restrained from penetrating beyond the second flexible axes of the flaps.

These four benefits are obtained because the sanitary napkin of the present invention bends along the axes of flexibility. The anatomical features of the crotch area of a woman are such that the crotch section is substantially trapezoidal shaped, with the center area of the crotch, which is located at the vaginal opening, being the base of the trapezoid. When a sanitary napkin of the present invention, such as the embodiment shown in FIGS. 1 and 2, is in use, the anatomical features of the crotch area force the sanitary napkin to bend upward at the first axis of flexibility. This results in the sanitary napkin forming a wall at each side of the central absorbent pad; the wall extends from the first axis of flexibility to the second axis of flexibility, as illustrated in FIG. 7. Thus, in use, the sanitary napkin of the present invention has a well-like shape with the plane formed by the second axes of flexibility (234 and 234') that are wrapped around the edge of the crotch portion of the panty (246 and 246') being higher than the plane formed by the first axes of flexibility (256 and 256') when the user is in an upright position.

Inherent bunching in the sanitary napkin of the present invention is substantially limited to the central absorbent pad; essentially no flow channels are formed in the walls. Without being bound by any theory, it is believed that when the flow channels are being formed, the energy creating them is transmitted across the central absorbent pad and the flow channels are extended. This proceeds until the flow channels reach the first axes of flexibility. The flow channels extend no farther than this because, it is believed, the first axes of flexibility relieve the energy extending the flow channels. Thus the flow channels will hot reach the gasket-like seal formed between the flap and the body at the second axis of flexibility, and, therefore, the seal will remain intact. The gasket-like seal forms a dam and blocks the flow of the menstrual fluid. The menstrual fluid can then be absorbed (or reabsorbed) by the absorbent core.

The sanitary napkin of the present invention can withstand much forced bunching before any flow channels are created, because the energy transmitted to the sanitary napkin by the forced bunching results in the walls tending to rotate around each first axis of flexibility. Without such rotation flow channels would be formed.

Even if the forced bunching is harsh enough to create flow channels, the channels will be substantially limited to the central absorbent pad. This is true for the same reasons that inherent bunching forms flow channels only in the central absorbent pad. Therefore, the gasket-like seal will remain intact and form a dam and block the flow of the menstrual fluid until it can be absorbed by the absorbent core.

Even if the forced bunching is so great that flow channels are created in both the central absorbent pad and the flaps, menstrual fluid is restrained from penetrating beyond the second axes of flexibility of the flaps. Such flow channels are likely to break the gasket-like seal. However, menstrual fluid is restrained from penetrating beyond the second flexible axes of the flaps because the walls themselves will form a barrier to flow of menstrual fluid. Menstrual fluid would have to flow up the walls, which is substantially directly against the force of gravity when the user is in an upright position, in order to penetrate the break in the gasket-like seal. Thus the walls themselves restrain the flow of the menstrual fluid.

In summary, the sanitary napkin of the present invention forms flow channels essentially only in the central absorbent pad which results in the gasket-like seal remaining intact. Thus, menstrual fluid will not flow beyond the gasket-like seal. However, if the forced bunching is so great that the gasket-like seal breaks, the walls themselves restrain the flow of the menstrual fluid.

It is important to note that only a minimal amount of flap absorbent core 230, or even no flap absorbent core at all, is not inimical to the prevention of soiling by the menstrual fluid. This is due to the fact that the primary function of the walls formed by the flaps is menstrual fluid containment rather than absorbency. The central absorbent means absorbs the vast majority of the menstrual fluid. Furthermore, a minimal amount of flap absorbent core is much less bulky and, therefore, more comfortable to the user.

It is also important to note that in FIG. 7 flap adhesive 236 is illustrated as contacting the edge of the panty only on its "outer" surface. While this is a preferred way of securing the sanitary napkin in the panty, flap adhesive can contact the edge of the panty on only its "inner" surface or both its "inner" and "outer" surfaces so long as a portion of the flap extends around and about the edge of the panty.

The sanitary napkin of this invention has been described as a device which has two flaps which, in use, each form a wall. While those embodiments are highly preferred, devices having only one flap can be envisioned. This one flap would be associated with the central absorbent means along a nonlinear line of juncture. The flap would contain at least two, and preferably at least four, axes of flexibility which would allow it to form both walls described above as it is folded completely around the crotch portion of a panty. The flap would then be associated with the central absorbent means along a nonlinear line of juncture opposite the one mentioned above.

In the embodiments of the sanitary napkin of this invention, illustrated and discussed above, adhesive attachment means were present near the distal edges of the flaps and in register with the central absorbent pad. These elements, designed to hold the sanitary napkin securely in the crotch region of an undergarment, are highly preferred elements. Without detracting from that position, it can be asserted that embodiments of the present invention which effectively lack one or more of the described adhesive attachment means are also useful, novel, effective devices.

The embodiment illustrated in FIGS. 1 and 2 can be readily adapted to function as an embodiment of the present invention which is effectively free of one or more of the adhesive attachment means.

For example, central pad adhesive 220 (and, naturally, its associated central pad release liner 222) can be omitted from sanitary napkin 210 illustrated in FIGS. 1 and 2. In use, this modified embodiment would be placed in the interior crotch region of a panty, just as the unmodified embodiment, except that central absorbent pad 220 is not secured to the interior crotch region of the panty. Flaps 224 and 224' can be secured about the elastic edge of the panty as described above with flap adhesive 236 and 236'. The panty with its associated modified sanitary napkin would then be donned by the user as before. Flap adhesive 236 and 236' in cooperation with the elastic edges of the panty hold the modified sanitary napkin in place.

In a like manner, sanitary napkin 210 can be modified by omitting only flap adhesive 236 and 236' (and release liners 238 and 238'). The modified sanitary napkin would be secured in the crotch region of the panty with central pad adhesive 220 and the flaps would be merely folded about the elastic edges.

In a like manner, sanitary napkin 210 can be modified by omitting all flap and central pad adhesives. In use, such a modified sanitary napkin would be maintained in position soley by cooperation among the flaps, the elastic edges of the panty, and the user's body.

Two points must be stressed in the immediately preceding discussion about modified embodiments of the present invention.

First, only adhesive attachment means are omitted from the modified sanitary napkins. All other necessary elements of the device—absorbent means, flaps, nonlinear lines of juncture, first and second axes of flexibility—are required.

Second, the modified sanitary napkins were described generally as being "effectively free" of adhesive attachment means. The state of being "effectively free" can be achieved by completely omitting adhesive attachment means during manufacture of the device as described. It can also be achieved by applying complete sanitary napkin 210, as illustrated in FIGS. 1 and 2, to the panty with one or more of the adhesive attachment means covered with release liner. Sanitary napkin 210 applied thusly would function essentially as if the covered adhesive attachment means were not present. The benefits of a totally or partially free floating sanitary napkin could then be obtained.

It will be understood by those skilled in the art that the invention has been described with reference to exemplary embodiments and that variations and modifications can be effected in the described embodiments without departing from the scope and spirit of the invention.

What is claimed is:

1. An absorbent article comprising:
   a) a central absorbent pad having longitudinal edges and a pair of flaps extending laterally outward from said longitudinal edges, said central absorbent pad having a body contacting surface and a garment surface, said flaps having a resistance to bending, through an arc of 90°, of between about 20 grams and about 200 grams; and
   b) attachment means for securing the absorbent article to an undergarment, said attachment means being positioned on each of said flaps.

2. The absorbent article of claim 1 wherein said flaps have a resistance to bending of between about 20 grams and about 70 grams.

3. The absorbent article of claim 1 wherein said body contacting surface of said central absorbent pad has a surface area between about 14.5 cm$^2$ (2.3 in$^2$) and about 83.4 cm$^2$ (12.9 in$^2$).

4. An absorbent article comprising:
   a) a liquid pervious topsheet;
   b) a liquid impervious backsheet;
   c) an absorbent core positioned between said topsheet and said backsheet;
      thereby forming a central absorbent pad having longitudinal edges and a pair of flaps extending laterally outward from said longitudinal edges, said central absorbent pad having a body contacting surface and a garment surface, said flaps having a resistance to bending, through an arc of 90°, of between about 20 grams and about 200 grams;
   d) attachment means for securing said pad to an undergarment, said attachment means being positioned on said garment surface on both of said flaps; and
   e) release paper covering said attachment means.

5. The absorbent article of claim 4 wherein each of said flaps has a width dimension such that said flaps do not contact one another when said flaps are folded under the undergarment.

6. The absorbent article of claim 4 wherein each of said flaps is designed to bend downward at an axis parallel to each of said longitudinal sides so that each said flap is to be secured to the exterior surface of the undergarment by said attachment means.

7. The absorbent article of claim 4 wherein said central absorbent pad is relatively thin.

8. The absorbent article of claim 4 wherein each of said flaps has a width of from about 1 cm to about 11 cm and a length of from about 7.6 cm to about 18 cm.

9. An absorbent article comprising:
   a) a liquid pervious topsheet;
   b) a liquid impervious backsheet;
   c) an absorbent core positioned between said topsheet and said backsheet;
      thereby forming a central absorbent pad with longitudinal edges and a pair of flaps, said central absorbent pad having a body contacting surface and a garment surface, said flaps having a resistance to bending, through an arc of 90°, of between about 10 grams and about 200 grams;
   d) adhesive attachment means for securing said central absorbent pad to an undergarment, said adhesive attachment means being positioned on said garment-facing surface with a portion of said adhesive attachment means being present on said central absorbent pad and a portion of each of said flaps; and
   e) a release liner covering said adhesive attachment means.

10. The absorbent article of claim 9 wherein said flaps, with said release liner removed, have a resistance to bending, through an arc of 90°, of between about 10 grams and about 100 grams.

11. The absorbent article of claim 9 wherein each of said flaps has a width of from about 1 cm to about 11 cm and a length of from about 7.6 cm to about 18 cm.

12. The absorbent article of claim 9 wherein said flaps, with said release liner removed, have a resistance to bending, through an arc of 90°, of between about 10 grams and about 100 grams.

13. An absorbent article comprising;
   a) a liquid pervious nonwoven topsheet;
   b) a liquid impervious polyethylene backsheet;
   c) an absorbent core positioned between said topsheet and said backsheet;
      thereby forming a central absorbent pad having longitudinal edges and a pair of lateral flaps extending outward from said longitudinal edges, each of said flaps having a length less than the length of said central absorbent pad, said central absorbent pad having a body contacting surface, a garment surface, said flaps having a resistance to bending, through an arc of 90°, of between about 20 grams and about 200 grams;
   d) adhesive attachment means for securing said pad to an undergarment, said adhesive attachment means being positioned on said garment surface with portions of said adhesive attachment means being positioned on said central absorbent pad and portions of said adhesive attachment means being positioned on each of said flaps; and
   e) release paper covering said adhesive attachment means.

14. The absorbent article of claim 13 wherein said central absorbent pad has an hourglass configuration.

15. The absorbent article of claim 13 wherein said central absorbent pad has a rectangular configuration.

16. The absorbent article of claim 13 wherein said adhesive attachment means in said central absorbent pad has the same width as said absorbent core.

17. An absorbent article comprising:
   a) a liquid pervious topsheet;
   b) a liquid impervious backsheet;
   c) an absorbent core positioned between said topsheet and said backsheet, said absorbent core having a pair of longitudinal side edges; and
   d) a pair of flaps extending outwardly from said longitudinal sides, each of said flaps containing an adhesive, each of said flaps having a stiffness defined as a resistance to bending, through an arc of 90°, of between about 0.05 grams and about 10 grams, and each of said flaps comprises a topsheet having a caliper of less than about 0.075 cm.

18. A sanitary napkin of the type for placement in an undergarment, the sanitary napkin comprising:

a) a central absorbent pad having longitudinal edges, said central absorbent pad having a body contacting surface and a garment surface;

b) a flap extending outwardly from each longitudinal edge of said central absorbent pad a length sufficient to be positioned around an edge of the undergarment, each said flap having a resistance to bending, through an arc of 90°, of between about 20 grams and about 200 grams; and c) attachment means for securing the sanitary napkin to the undergarment when each of said flaps are positioned around an edge of the undergarment, said attachment means being positioned on each of said flaps.

19. The sanitary napkin of claim 18 wherein said flaps have a resistance to bending of between about 20 grams and about 70 grams.

20. A sanitary napkin of the type for placement in an undergarment, the sanitary napkin comprising:

a) a liquid pervious topsheet;

b) a liquid impervious backsheet;

c) an absorbent core positioned between said topsheet and said backsheet;

thereby forming a central absorbent pad having longitudinal edges and a pair of flaps extending outwardly from each longitudinal edge of said central absorbent pad a length sufficient to be positioned around an edge of the undergarment, said central absorbent pad having a body contacting surface and a garment surface, said flaps having a resistance to bending, through an arc of 90°, of between about 20 grams and about 200 grams;

d) attachment means for securing the sanitary napkin to the undergarment when each of said flaps are positioned around an edge of the undergarment, said attachment means being positioned on said garment surface on both of said flaps; and e) release paper covering said attachment means.

21. The absorbent article of claim 20 wherein each of said flaps has a width dimension such that said flaps do not contact one another when said flaps are folded under the undergarment.

22. The absorbent article of claim 21 wherein each of said flaps has a width of from about 1 cm to about 11 cm and a length of from about 7.6 cm to about 18 cm.

23. The absorbent article of claim 20 wherein each of flaps is designed to bend at an axis parallel to each of said longitudinal edges so that each said flap is to be secured to the exterior surface of the undergarment by said attachment means.

24. The absorbent article of claims 20 wherein said central absorbent pad is relatively thin.

25. A sanitary napkin of the type for placement in an undergarment, the sanitary napkin comprising:

a) a liquid pervious topsheet;

b) a liquid impervious backsheet;

c) an absorbent core positioned between said topsheet and said backsheet;

thereby forming a central absorbent pad with longitudinal edges and a pair of flaps extending from each longitudinal edge wherein said flaps extend to a length sufficient to allow each of said flaps to be positioned around an edge of the undergarment, said central absorbent pad having a body contacting surface and a garment surface, said flaps having a resistance to bending, through an arc of 90°, of between about 10 grams and about 200 grams;

d) adhesive attachment means for securing the sanitary napkin to the undergarment, said adhesive attachment means being positioned on said garment facing surface with a portion of said adhesive attachment means being present on said central absorbent pad and a portion on each of said flaps; and e) a release liner covering said adhesive attachment means.

26. The sanitary napkin of claim 25 wherein said flaps, with said release liner removed, have a resistance to bending, through an arc of 90°, of between about 15 grams and about 70 grams.

27. The absorbent article of claim 25 wherein each of said flaps has a modified trapezoidal shape.

28. The sanitary napkin of claim 27 wherein each of said flaps has a width of from about 1 cm to about 11 cm and a length of from about 7.6 cm to about 18 cm.

29. A sanitary napkin of the type for placement in an undergarment, the sanitary napkin comprising:

a) a liquid pervious nonwoven topsheet;

b) a liquid impervious polyethylene backsheet;

c) an absorbent core positioned between said topsheet and said backsheet;

thereby forming a central absorbent pad having longitudinal edges and a pair of lateral flaps extending outward from said longitudinal edges and having a length sufficient to allow each of said flaps to be positioned around an edge of the undergarment, each of said flaps having a length less than the length of said central absorbent pad, said central absorbent pad having a body contacting surface, a garment surface, said flaps having a resistance to bending, through an arc of 90°, of between about 20 grams and about 200 grams;

d) adhesive attachment means for securing the sanitary napkin to the undergarment, said adhesive attachment means being positioned on said garment surface with portions of said adhesive attachment means being positioned on said central absorbent pad and portions of said adhesive attachment means being positioned on each of said flaps; and e) release paper covering said adhesive attachment means.

30. The sanitary napkin of claim 29 wherein said central absorbent pad has an hourglass configuration.

31. The absorbent article of claim 30 wherein said central absorbent pad has a rectangular configuration.

32. The absorbent article of claim 31 wherein said adhesive attachment means in said central absorbent pad has the same width as said absorbent core.

33. A sanitary napkin of the type for placement in an undergarment, the sanitary napkin comprising:

a) a liquid pervious topsheet;

b) a liquid impervious backsheet;

c) an absorbent core positioned between said topsheet and said backsheet, said absorbent core having a pair of longitudinal side edges; and d) a pair of flaps extending outwardly from said longitudinal sides and having a length sufficient to allow each of said flaps to be positioned around an edge of the crotch portion of the undergarment, each of said flaps containing an adhesive, each of said flaps having a stiffness defined as a resistance to bending, through an arc of 90°, of between about 0.05 grams and about 10 grams, and each of said flaps comprises a topsheet having a caliper of less than about 0.075 cm.

* * * * *